United States Patent
Lefebvre et al.

(10) Patent No.: US 11,254,833 B2
(45) Date of Patent: Feb. 22, 2022

(54) COATING COMPOSITION BASED ON COLORING FOODSTUFFS

(71) Applicant: SOCIETE D'EXPLOITATION DE PRODUITS POUR LES INDUSTRIES CHIMIQUES SEPPIC, Paris (FR)

(72) Inventors: Sandra Lefebvre, Castres (FR); Philippe Rouanet, L'albarede Guitalens (FR)

(73) Assignee: SOCIETE D'EXPLOITATION DE PRODUITS POUR LES INDUSTRIES CHIMIQUES SEPPIC, Paris (FR)

( * ) Notice: Subject to any disclaimer, the term of this patent is extended or adjusted under 35 U.S.C. 154(b) by 119 days.

(21) Appl. No.: 14/774,497

(22) PCT Filed: Mar. 12, 2014

(86) PCT No.: PCT/FR2014/050565
§ 371 (c)(1),
(2) Date: Sep. 10, 2015

(87) PCT Pub. No.: WO2014/140482
PCT Pub. Date: Sep. 18, 2014

(65) Prior Publication Data
US 2016/0032128 A1 Feb. 4, 2016

(30) Foreign Application Priority Data

Mar. 13, 2013 (FR) ...................................... 1352237

(51) Int. Cl.
| | | |
|---|---|---|
| *C09D 101/00* | (2006.01) | |
| *C09D 101/28* | (2006.01) | |
| *A23G 3/34* | (2006.01) | |
| *A23G 1/30* | (2006.01) | |
| *A23G 4/06* | (2006.01) | |
| *A61K 9/28* | (2006.01) | |
| *A23G 1/48* | (2006.01) | |
| *A23L 5/42* | (2016.01) | |
| *A23P 20/10* | (2016.01) | |
| *B05D 1/02* | (2006.01) | |
| *C08K 5/101* | (2006.01) | |

(52) U.S. Cl.
CPC ......... *C09D 101/284* (2013.01); *A23G 1/305* (2013.01); *A23G 1/48* (2013.01); *A23G 3/343* (2013.01); *A23G 4/062* (2013.01); *A23L 5/42* (2016.08); *A23P 20/105* (2016.08); *A61K 9/288* (2013.01); *B05D 1/02* (2013.01); *C08K 5/101* (2013.01)

(58) Field of Classification Search
None
See application file for complete search history.

(56) References Cited

U.S. PATENT DOCUMENTS

| | | | |
|---|---|---|---|
| 4,513,019 A | 4/1985 | Brancq et al. | |
| 5,194,278 A * | 3/1993 | Strong | A23L 25/25 426/293 |
| 5,393,333 A | 2/1995 | Trouve | |
| 10,736,335 B2 * | 8/2020 | Mo | A23G 4/068 |
| 2005/0147724 A1 | 7/2005 | Schweinfurth | |
| 2007/0202222 A1 | 8/2007 | Koenig et al. | |
| 2010/0254962 A1 * | 10/2010 | Zehethofer | A61K 36/45 424/94.1 |
| 2011/0280942 A1 * | 11/2011 | Schad | A61K 9/2813 424/476 |
| 2012/0260932 A1 * | 10/2012 | Marino | A61K 8/8141 132/200 |

FOREIGN PATENT DOCUMENTS

| | | | | |
|---|---|---|---|---|
| CN | 101190012 A * | 6/2008 | | |
| EP | 0 542 510 A1 | 5/1993 | | |
| EP | 1 764 003 A1 | 3/2007 | | |
| FR | 2 548 675 A1 | 1/1985 | | |
| FR | 2 660 317 A1 | 10/1991 | | |
| WO | 2006/066389 A1 | 6/2006 | | |
| WO | WO-2010052727 A1 * | 5/2010 | | A61K 9/286 |
| WO | 2011/089248 A1 | 7/2011 | | |
| WO | WO-2012078021 A * | 6/2012 | | C08L 99/00 |

OTHER PUBLICATIONS

Kopelman et al, Drum dried beet powder, J. Fd Technol. 12, pp. 615-621 (Year: 1977).*
Prior Art Web Search (Year: 2020).*
Tan et al, mixed polymer coating for modified release from coated spheriods, 1999 (Year: 1999).*
CN-101190012-A—English translation (Year: 2008).*
International Search Report, dated May 30, 2014, from corresponding PCT application.

* cited by examiner

*Primary Examiner* — Stefanie J Cohen
(74) *Attorney, Agent, or Firm* — Nixon & Vanderhye

(57) ABSTRACT

A coating composition includes, in relation to 100% of the weight thereof: between 10 and 90 wt. % of at least one film-forming polymer selected from cellulosic polymers or derivatives of cellulosic polymers, derivatives of vinyl alcohol, derivatives of vinyl pyrrolidones, polymers of a natural origin, acrylic or methacrylic derivatives, derivatives of glycol or propylene glycol or combinations of the two substances or the copolymers of vinyl alcohol and polyethylene glycol (PEG); between 1 and 50 wt. % of at least one food colouring agent; and between 0 and 50 wt. % of at least one auxiliary coating agent selected from white opacifiers, diluents, surfactants, plasticizers, and anti-foaming agents.

10 Claims, No Drawings

COATING COMPOSITION BASED ON COLORING FOODSTUFFS

The subjects of the present invention are coating compositions intended for the colored coating of ingestible solid forms, and more particularly of pharmaceutical, veterinary or dietary supplement tablets, processes for preparing said coating compositions, coating processes which employ said coating compositions, and colored coated products obtained by carrying out the coating processes comprising the use of said coating compositions.

The dry forms used in the industries of human or veterinary pharmaceuticals and of dietary supplements are generally in the form of tablets, gel capsules, sugar-coated tablets or granules which are made by agglomeration of solid particles comprising at least one active principle and/or at least one nutritional ingredient and at least one excipient. These dry forms may be prepared by employing numerous techniques known to those skilled in the art, such as, for example, techniques of compression, granulation, compacting or extrusion.

In order to protect these dry forms from degradation caused by external conditions, such as, for example, the degradation of the active principles contained in said dry forms by light radiation, or else from abrasion during the packaging thereof, or else from dust formation, and/or in order to improve the outer appearance of said dry forms by imparting a specific color or enhanced shine to them, said dry forms are covered in a film of a chemical composition serving as coating agent.

Coating compositions are well known to those skilled in the art and are generally composed of at least one film-forming agent and a coloring system composed of pigments of mineral origin, such as, for example, iron oxides, or composed of dyes.

Azo dyes are commonly used as coloring agents in the preparation of a coating composition, to impart a bright color to the film formed on the dry form.

Recent changes in European regulations relating to the use of azo dyes have led manufacturers to seek an alternative and to develop systems for coloring coating compositions which impart a bright color, are light-stable over time, and do not contain azo derivatives.

What are referred to as "natural" dyes may constitute an alternative to azo dyes. Most natural dyes are obtained by selective extraction of coloring molecules present in fruit and vegetables. By way of example, mention may be made of anthocyans, carotenoids, etc. They enable bright colors to be obtained but the light stability of these colors, imparted to the dry forms by these dyes, is often mediocre.

Based on European Directive No. 1334/2008, which defines natural flavorings used in food, the professional body NATCOL (Natural Food Colors Association) suggests classifying natural dyes as a function of how they are obtained by transposing the directive to dyes in order to establish clear definitions. These same definitions will be used in the present patent application.

This classification comprises two classes: dyes which are not present in nature and dyes which are present in nature. Among the latter, the classification makes a distinction between coloring substances obtained by chemical synthesis and coloring substances obtained by carrying out processes which use natural sources as starting materials, such as, for example, starting materials of animal, vegetable or mineral origin, used in processes of extraction and/or distillation and/or enzymatic fermentation.

Among these natural dyes, which are present in nature and are obtained from natural starting materials, mention may thus be made of anthocynanins (E163), chlorophylls (E140), carotenoids (E160a), curcumin (E100), lutein (E161b), lycopene (E160b) and paprika extracts (E160c).

However, the use of these natural dyes, which are present in nature and are obtained from natural starting materials, in the preparation of a film-coating composition does not enable colors which are stable over prolonged exposure to light to be imparted to the dry form coated with said film-coating composition.

Patent application WO 2011/089248 discloses compositions comprising:

a) an aqueous phase comprising water, at least one cosolvent selected from the group composed of propylene glycol, ethanol, triacetin and glycerol and optionally at least one sugar selected from the group composed of sucrose, fructose and glucose;

b) a surfactant system comprising at least one saponin and lecithin; and c) an oil phase comprising at least one substance selected from the group composed of flavorings, vitamins, dyes and polyunsaturated fatty acids.

These compositions are used to prepare food compositions (food and drinks).

The description of this patent application discloses preferred dyes: carotenoids, luteins and paprika extracts.

Patent application US 2007/0202222 discloses a food casing comprising a textile material and/or regenerated cellulose which are impregnated or coated, on their inside, with at least one dye.

The coloring foodstuffs described are in particular paprika, chicory, spices, caramel and tomato extracts.

Patent application WO 2006/066389 describes and claims compositions in the form of dry capsules comprising an insoluble matrix comprising at least 70 wt % proteins, between 5 and 10% water and an encapsulated active agent, characterized in that said matrix, once wetted in a colorless aqueous solution or a mineral oil, has a colorimetric component L* of lightness which is greater than 40, a colorimetric value C* of color saturation which is less than or equal to 33 and a "hue angle" between 70° and 90°.

The inventors of the present invention have thus sought to develop compositions intended for coating dry forms, providing a colored film on the latter, the color of which has a high intensity, which remains stable after prolonged exposure to light, with these coating compositions having to be devoid of azo-type dyes.

According to a first aspect, a subject of the invention is a coating composition comprising, per 100% of the weight thereof:

from 10 wt % to 90 wt %, preferably from 30 wt % to 80 wt % of at least one film-forming polymer selected from the cellulosic polymers or derivatives of cellulosic polymers, derivatives of vinyl alcohol, derivatives of vinylpyrrolidones, polymers of natural origin, acrylic or methacrylic derivatives, glycol or propylene glycol derivatives or combinations of these two substances, or vinyl alcohol-polyethylene glycol (PEG) copolymers, from 1 wt % to 50 wt %, preferably from 10 wt % to 40 wt %, of at least one coloring foodstuff, and from 0 to 50 wt %, preferably from 0 to 40 wt %, of at least one auxiliary coating agent selected from white opacifiers, diluents, surfactants, plasticizers and antifoams.

According to one specific aspect, a subject of the invention is a composition as defined above, characterized in that said at least one film-forming polymer is selected from methyl cellulose, hydroxypropylmethyl cellulose, hydroxypropyl cellulose, hydroxyethyl cellulose, sodium carboxymethyl cellulose, ethyl cellulose, PVAs (polyvinyl alcohols), PVA-PEG (polyethylene glycol) copolymers, polyvinyl acetate, polyvinylpyrrolidones (PVPs), vinylpyrrolidone-vinyl acetate copolymers, starches, maltodextrin-modified starches, alginates, pectin, gum arabic, guar gum, carrageenans, xanthan gum, inulin, chitosan, methacrylic acid-ethyl acetate copolymer, or the polyethylene glycol-polypropylene glycol (PEG-PPG) copolymer.

According to one specific aspect, a subject of the invention is a composition as defined above, characterized in that said at least one auxiliary coating agent is selected from white opacifiers such as titanium dioxide, talc, kaolin, magnesium oxide; diluents such as lactose, sucrose, mannitol, sorbitol, xylose, xylitol, isomalt, cellulose, talc, native starches; surfactants such as sorbitan esters, ethoxylated sorbitan esters, hydrogenated and ethoxylated castor oils, lecithins, sodium lauryl sulfate, ethoxylated fatty alcohols, ethoxylated fatty acids; plasticizers such as glycerin, polypropylene glycols, polyethylene glycols or derivatives thereof from condensation with a fatty acid or fatty alcohol, stearic acid and derivatives thereof, acetylated monoglycerides; and antifoams such as fatty acids or silicone derivatives.

According to one specific aspect, a subject of the invention is a composition as defined above, characterized in that said at least one coloring foodstuff is selected from concentrated fruit and vegetables, such as, for example, safflower, seaweed, carrot, purple carrot, black carrot, hibiscus, radish, blackcurrant, apple, lemon, spinach, grapes, blackcurrant, red cabbage, elderberries, beetroot, pumpkin, squash, nettles, turmeric, saffron, red berries and paprika.

According to one specific aspect, a subject of the invention is a composition as defined above, characterized in that it comprises from 10 wt % to 40 wt % coloring foodstuffs. Preferably, it comprises from 10 wt % to 30 wt % coloring foodstuffs.

Food colors, which require approval according to European regulation, should be distinguished from coloring foodstuffs which do not require this regulatory approval and which are employed in the composition forming the subject of the present invention.

The definition of the term "coloring foodstuff" is established as a function of the way in which said foodstuff is obtained. Specifically, obtaining a coloring foodstuff must not consist of selective extraction of coloring substances; moreover, the coloring foodstuff must retain its organoleptic characteristics, namely its flavor, taste and color. For example, a puree of spinach resulting from cooking, grinding, drying or concentrating spinach employed in its plant form, and used to obtain a green color, is a coloring foodstuff.

Coloring foodstuffs are concentrated fruit and vegetables having a coloring property. They are classed as ingredients and not additives. In particular, they have the following properties:
originating from edible plants,
physical processing involving only water as solvent,
no selective extraction of the coloring material,
no addition of functional additives.

In the prior art, nothing discloses nor suggests the use of coating compositions comprising coloring foodstuffs in association with at least one film-forming agent to improve the stability of the color intensity of a solid form coated with said coating compositions (intended for food, veterinary or pharmaceutical use) during prolonged exposure to light compared to the same solid form coated with a coating composition comprising a food color or a colored pigment.

However, surprisingly, the use of these concentrated fruit and vegetables in coating compositions enables bright colors to be obtained, which are more stable than those obtained with coating compositions comprising natural dyes extracted selectively from fruit and vegetables.

According to another specific aspect, a subject of the invention is a coating composition as defined above, characterized in that it is in a ready-to-use form containing mixtures of its various constituents in the form of an aqueous dispersion, a powder or ready-to-use granules.

The term "aqueous dispersion" is understood as dispersions produced in water or mixtures of water and water-soluble alcohols such as, for example, ethanol.

Ready-to-use compositions have several advantages:
Handling, storage and checking of just one product.
Better reproducibility of colors and performance.
Easier dispersion.

Another subject of the invention is a process for preparing a coating composition as defined above and which is in the form of a dry powder, comprising the following steps:
a step (a) of mixing the film-forming polymer, coloring foodstuff and, if necessary or desired, one or more other auxiliary coating agents,
an optional step (b) of milling the mixture arising from step (a) to form said coating composition.

In the process as defined above, all the components are added sequentially or simultaneously in order to carry out step (a).

Mixing is then generally carried out with a powder mixer of the paddle mixer, tumbler mixer or V-mixer type.

Step (b) of the process as defined above is, for example, carried out by means of a knife mill or a pin mill, so as to obtain a finely divided powder, or with a cryo-grinding device generally under liquid nitrogen.

Such a device enables the final particle size of the coating composition to be optimized.

Another subject of the invention is a process for preparing a coating composition as defined above and which is in the form of ready-to-use granules, comprising the following steps:
a step (a1) of wetting the mixture of film-forming polymer, coloring foodstuff and, if necessary or desired, one or more other auxiliary coating agents using a binder solution, so as to obtain a wet mass containing from 30% to 60% water,
a step (b1) of drying the wet mass obtained in step (a1) and, if desired or necessary,
a step (c1) of calibrating the dried mass obtained in step (b1) to obtain said coating composition.

The process as defined hereinabove is for example described in the French patent applications published under the numbers FR 2 548 675 and FR 2 660 317 or in the Kirk-Othmer encyclopedia ($3^{rd}$ edition, volume 17, page 281).

The term "granules" is understood mainly as agglomerates of several tens to several thousands of initially individual particles of material which may be of identical or different nature.

Steps (a1) and (b1) of the process as defined hereinabove are in particular carried out in a mixer/granulator or in a fluidized bed.

Step (c1) of the process as defined above is in particular carried out in an oven or in a fluidized bed.

Another subject of the invention is a process for preparing a coating composition as defined above and which is in the form of an aqueous dispersion, comprising the following steps:

a step (a2) of dispersing, in an aqueous phase, the film-forming polymer, the coloring foodstuff and, if necessary or desired, one or more other auxiliary coating agents, a step (b2) of milling the mixture arising from step (a1) to form said coating composition.

Another subject of the invention is the use of the coating composition as defined above for coating ingestible solid forms.

The term "ingestible solid form" is used to denote solid forms which are ingestible by humans or animals, irrespective of their purpose, whether as medicaments, dietary supplements, forms intended for cosmetic use, confectionery or candy. The use of the coating composition as defined above is more particularly intended for tablets.

Another subject of the invention is a process for coating edible solid forms, comprising:

a step (a3) of dispersing, in a suitable solvent such as an aqueous medium, the mixture containing the film-forming polymer, the coloring foodstuff and, if necessary or desired, the other auxiliary coating agents;

a step (b3) of spraying the dispersion obtained in step (a3) onto solid substrates to be coated.

In step (a3) of the process as defined above, the various constituents are kept in dispersion by means of a mixer and a deflocculating impeller, or a blade of "boat" type, while avoiding foam formation.

In step (a3) of the process as defined above, the coating composition represents from 6 wt % to 30 wt %, more particularly from 6 wt % to 25 wt %, and even more particularly from 6 wt % to 20 wt % per 100% of the weight of said dispersion.

Preparation of the Dispersions

The coating compositions are dispersed at 25 wt % in water. For each composition, 600 g of dispersion are prepared: 150 g of composition are dispersed in 450 g of purified water at 25° C. The dispersing is carried out by means of a laboratory mixer of the Turbotest V2004 type (sold by Rayneri) and a deflocculating impeller. The mixing speed is adjusted to avoid incorporating air into the dispersion, which avoids foam formation. After 45 minutes of mixing, the dispersions are ready.

Film-Coating

The dispersions are sprayed onto placebo tablets in a Driacoater 500 perforated film-coating pan sold by DRIAM; the load of cores in the pan is 3 kg. The following operating conditions are followed: air flow=300 m³/h, input temperature of drying air: 55° C.-60° C. The temperature of the cores varies between 36° C.-38° C. during the film-coating operation. A theoretical dry deposit of 3% is applied to the tablets.

The use of the coating composition, according to the above-described processes, enables coated pharmaceutical, veterinary or dietary supplement tablets to be prepared. The following examples illustrate the invention in a nonlimiting manner.

EXAMPLES

Example 1

Coating Compositions, the Constituents of which are Expressed as Weight Percentages, are Formulated as Follows

|  | Comparative example: composition A | Inventive composition: composition B |
|---|---|---|
| Film-forming agent | Hydroxypropylmethyl cellulose (HPMC): 69.8% Carboxymethyl cellulose (CMC): 12.2% | Hydroxypropylmethyl cellulose (HPMC): 69.8% Carboxymethyl cellulose (CMC): 12.2% |
| Auxiliary agent | Acetylated monoglycerides: 6% | Acetylated monoglycerides: 6% |
| Coloring system | 12% natural dye: carotenoids. (β-carotene powder: Fusion Red Orange P-WD. CAS number: 7235-40-7) | 12% coloring foodstuff: black carrots |

500 mg tablets comprising, per 100% of their weight, 49.75 wt % microcrystalline cellulose, 49.75 wt % lactose and 0.5 wt % magnesium stearate are coated with coating compositions A and B.

Coating is carried out in a perforated "PILOT XT laboratory tablet coater" pan sold by Profile Automation, loaded with 2 kg of tablets.

At the end of the prior coating step, the coated tablets obtained are then placed in daylight and darkness so as to measure the stability of the coloring.

The color of the tablets is monitored regularly using a MEDSCAN colorimeter, sold by NEWTONE.

| Composition coating the tablet | L*a*b* of tablets at T = 0 | L*a*b* of tablets after 2 weeks in light | L*a*b* of tablets after 5 weeks in light | L*a*b* of tablets after 7 weeks in light |
|---|---|---|---|---|
| Composition A | 64.4/57.9/ 59.8 | 74.4/25.9/ 67.2 | 92.9/−0.4/ 4.6 (total loss of color of tablet) | No stability |
| Composition B | 42.4/33.6/ −0.8 | 44.5/36.0/ 0.0 | 48.2/34.5/ 0.0 (color of tablets very close to T = 0) | 50.3/32.2/ 0.0 (color of tablets close to T = 0) |

Interpretation in terms of color saturation, according to the saturation C* parameter, calculated according to the formula: $C^* = (a^{*2} + b^{*2})^{1/2}$.

| Composition coating the tablet | Saturation C* at T = 0 | Saturation C* after 2 weeks in light | Saturation C* after 5 weeks in light | Saturation C* after 7 weeks in light |
|---|---|---|---|---|
| Composition A | 83.2 | 72.0 | 4.6 | No stability |
| Composition B | 33.6 | 36.0 | 34.5 | 32.2 |

The coating composition B comprising the coloring foodstuff enables tablets to be obtained, the color of which remains intense and stable for at least 7 weeks in daylight.

Conversely, significant loss of color is observed for the tablets coated by composition A comprising carotenoids.

Example 2

Coating Compositions, the Constituents of which are Expressed as Weight Percentages and which are More Concentrated in Dyes/Coloring Foodstuffs, were Prepared and are Formulated as Follows

|  | Comparative example: composition C | Comparative example: composition D | Inventive composition: composition E |
|---|---|---|---|
| Film-forming agent | Hydroxypropylmethyl cellulose (HPMC): 59% Carboxymethyl cellulose (CMC): 11% | Hydroxypropylmethyl cellulose (HPMC): 59% Carboxymethyl cellulose (CMC): 11% | Hydroxypropylmethyl cellulose (HPMC): 59% Carboxymethyl cellulose (CMC): 11% |
| Coloring | 30% natural dye: carotenoids. (β-carotene powder; Fusion Red Orange P-WD. CAS number: 7235-40-7) | 30% natural dye: carotenoids. (Natracol beta carotene wsp. CAS number: 7235-40-7) | 30% coloring food-stuffs: purple carrots. |

500 mg tablets comprising, per 100% of their weight, 49.75 wt % microcrystalline cellulose, 49.75 wt % lactose and 0.5 wt % magnesium stearate are coated with coating compositions C, D and E. Coating is carried out in a perforated "PILOT XT laboratory tablet coater" pan sold by Profile Automation, loaded with 2 kg of tablets.

At the end of the prior coating step, the coated tablets obtained are then placed, for stability purposes, in daylight and darkness. The color of the tablets is monitored regularly using a MEDSCAN colorimeter, sold by NEWTONE.

| Composition coating the tablet | L*a*b* of tablets at T = 0 | L*a*b* of tablets after 2 weeks in light | L*a*b* of tablets after 5 weeks in light | L*a*b* of tablets after 5 weeks in the dark | L*a*b* of tablets after 6 months in light | L*a*b* of tablets after 6 months in the dark |
|---|---|---|---|---|---|---|
| Composition C | 58.8/53.1/52.5 | 67.6/47.2/55.2 | 84.8/−1.5/65.3 (loss of color of tablet) | 66.3/51.4/63.1 | No stability | No stability |
| Composition D | 67.8/46.9/65.1 | 75.5/19.6/74.0 | 84.4/−3.7/75.1 (loss of color of tablet) | 75.0/21.3/75.1 | No stability | No stability |
| Composition E | 58.7/50.7/28.2 | 62.3/46.5/23.8 | 62.2/46.0/19.0 | 62.8/48.1/22.8 | 66.7/42.3/19.2 | 62.8/47.5/21.3 |

As above, the coating composition E according to the invention, comprising the coloring foodstuff, enables a color for the tablets to be obtained which is intense and stable for 6 months in daylight. Moreover, the L*a*b* parameters measured after 6 months in light for the tablets coated with composition E show very little difference to the L*a*b* parameters measured after 6 months in darkness.

On the contrary, a rapid loss of color is observed for the tablets coated with compositions C and D, comprising carotenoids as coloring system. Therefore, the results do not depend on the amount of dye used.

The parameters used to describe a color can be subsumed under three categories:
hue, which characterizes the color itself (green, red, etc.)
lightness, which characterizes the ability of the colored sample to reflect light to a greater or lesser extent (light color, dark color, etc.)
saturation, which characterizes the intensity of color of the sample (bright color=saturated color).

The CIELab 1976 system is used to mathematically represent the colorimetric coordinates of a color.

This system has two modes of representation:
Representation by L*a*b* coordinates in which L* represents the lightness axis, a* the red/green axis and b* the yellow/blue axis.
Representation by L*C*h0 coordinates in which L* represents the lightness axis, C* the saturation axis and h0 the hue angle.

In order for a color to be stable, the variation of the L*a*b* or L*C*h0 over time must be as small as possible.

The L*a*b* coordinates were used for the examples of the present invention.

The invention claimed is:

1. A coating composition comprising, per 100% of the weight thereof:
from 70 wt % to 82 wt % of a film-forming polymer combination of hydroxypropylmethyl cellulose and sodium carboxymethyl cellulose, wherein the hydroxypropylmethyl cellulose comprises between 59% and 69.8% and the sodium carboxymethyl cellulose comprises between 11% and 12.2%,
from 12 wt % to 30 wt % of at least one coloring foodstuff, said at least one coloring foodstuff comprising concentrated black carrot or purple carrot prepared with physical processing using only water as a solvent,
wherein the at least one coloring foodstuff does not contain any functional additives,
wherein the at least one coloring foodstuff retains a flavor, a taste and a color of said at least one coloring foodstuff and said at least one coloring foodstuff does not consist of selective extraction of a coloring substance from said at least one coloring foodstuff, and
from 0 to 6 wt % of at least one auxiliary coating agent selected from the group consisting of white opacifiers, diluents, surfactants, plasticizers and antifoams,
wherein the intensity and stability, as measured by L*a*b* coordinates, of the color of the coloring foodstuff is maintained after six months in daylight by approximately at least 88%, 83%, and 75% respectively for the L*a*b* coordinates.

2. The coating composition as claimed in claim 1, wherein said at least one auxiliary coating agent is selected from the group consisting of:
white opacifiers selected from the group consisting of titanium dioxide, talc, kaolin, and magnesium oxide;
diluents selected from the group consisting of lactose, sucrose, mannitol, sorbitol, xylose, xylitol, isomalt, cellulose, talc, and native starches;
surfactants selected from the group consisting of sorbitan esters, ethoxylated sorbitan esters, hydrogenated and ethoxylated castor oils, lecithins, sodium lauryl sulfate, ethoxylated fatty alcohols, and ethoxylated fatty acids;

plasticizers selected from the group consisting of glycerin, polypropylene glycols, polyethylene glycols or derivatives thereof from condensation with a fatty acid or fatty alcohol, stearic acid and derivatives thereof, and acetylated monoglycerides; and antifoams selected from the group consisting of fatty acids and silicone derivatives.

3. The coating composition as defined in claim 1, wherein said composition is in the form of an aqueous dispersion, a powder or ready-to-use granules.

4. A process for preparing the coating composition as defined in claim 1 and which is in the form of a dry powder, comprising the following steps:
- a step (a) of mixing the film-forming polymer combination, coloring foodstuff and, optionally, one or more other auxiliary coating agents to form a mixture,
- an optional step (b) of milling the mixture arising from step (a) to form said coating composition.

5. A process for preparing a coating composition as defined in claim 1 and which is in the form of ready-to-use granules, comprising the following steps:
- a step (a1) of wetting a mixture of film-forming polymer combination, coloring foodstuff and, optionally, one or more other auxiliary coating agents using a binder solution, so as to obtain a wet mass containing from 30% to 60% water,
- a step (b1) of drying the wet mass obtained in step (a1) to obtain a dried wet mass and, optionally,
- a step (c1) of calibrating the dried wet mass obtained in step (b1) to obtain said coating composition.

6. A process for preparing the coating composition as defined in claim 1 and which is in the form of an aqueous dispersion, comprising the following steps:
- a step (a2) of dispersing, in an aqueous phase, the film-forming polymer combination, the coloring foodstuff and, optionally, one or more other auxiliary coating agents,
- a step (b2) of milling the dispersion obtained from step (a2) to form said coating composition.

7. A process for coating ingestible solid forms comprising coating the ingestible solid forms with an effective amount of the coating composition as defined in claim 1.

8. A process for preparing coated solid forms comprising:
dispersing in an aqueous medium the coating composition as defined in claim 1; and
spraying the dispersion obtained onto solid substrates to be coated.

9. The coating composition as defined in claim 1, wherein:
said at least one auxiliary coating agent is a plasticizer selected from the group consisting of glycerin, polypropylene glycols, polyethylene glycols or derivatives thereof from condensation with a fatty acid or fatty alcohol, stearic acid and derivatives thereof, and acetylated monoglycerides.

10. The coating composition as defined in claim 1 wherein the stability of the intensity, as measured by L*a*b* coordinates, of the color of the coloring foodstuff is substantially greater as compared to the same composition using from 12 wt % to 30 wt % of a carotenoid natural dye instead of the at least one coloring foodstuff.

* * * * *